United States Patent [19]

Barnett, Jr. et al.

[11] Patent Number: 5,268,177
[45] Date of Patent: Dec. 7, 1993

[54] METHOD FOR REDUCING DEFLAGRATION OF AZINPHOS-METHYL

[75] Inventors: Horace G. Barnett, Jr., Kansas City; Christopher M. Tusa, Grandview, both of Mo.

[73] Assignee: Miles Inc., Pittsburgh, Pa.

[21] Appl. No.: 563,371

[22] Filed: Aug. 6, 1990

[51] Int. Cl.$^5$ .............................................. A01N 25/18
[52] U.S. Cl. ..................................... 424/405; 424/40; 424/41
[58] Field of Search ........................... 424/40, 41, 405

[56] References Cited

U.S. PATENT DOCUMENTS

| 2,842,477 | 7/1958 | Ellern et al. | 424/41 |
| 3,856,933 | 12/1974 | Jankowiak et al. | 424/40 |
| 4,199,548 | 4/1980 | Kaiho et al. | 424/40 |

FOREIGN PATENT DOCUMENTS 6339803 10/1977 Japan.

*Primary Examiner*—Thurman K. Page
*Assistant Examiner*—Robert H. Harrison
*Attorney, Agent, or Firm*—Joseph C. Gil; Lyndanne M. Whalen

[57] ABSTRACT

A carbonate of an alkali metal is added to an azinphos-methyl powder formulation in an amount such that the carbonate is at least 10% by weight of the total mixture. Sodium bicarbonate is the preferred carbonate. The resultant mixtures are characterized by a reduced tendency toward deflagration at temperatures below 200° C.

8 Claims, No Drawings

METHOD FOR REDUCING DEFLAGRATION OF AZINPHOS-METHYL

BACKGROUND OF THE INVENTION

The present invention relates to an azinphos-methyl powder insecticide composition characterized by an elevated deflagration temperature and a reduced tendency to undergo exothermic decomposition.

Insecticides are used in a variety of forms. One form useful for treating enclosed, limited spaces is as a fumigant. Japanese Patent 63039803, for example, teaches an insecticide fumigant which undergoes controlled decomposition. In this fumigant, the insecticide is mixed with a thermodecomposable compound that will produce nitrogen and carbon dioxide at temperatures less than 300° C. Among the thermodecomposable compounds taught to be appropriate are ammonium salts, metal azides, inorganic carbonates and organic carboxylic acids. These thermodecomposable compounds are used in quantities such that they constitute at least 50% by weight of the fumigant mixture.

Insecticides for more open areas are generally applied by spraying. Sprays can be produced by either diluting liquid concentrates or by adding liquid to an insecticide in wettable powder form. The wettable powder forms are generally preferred because they are much easier to ship and store. The dry powder is also less likely to penetrate the clothing and skin of the person handling it than a liquid concentrate. It is also easier to clean up a powder than a liquid in the event of a spill. However, insecticides such as azinphos-methyl which are in powder form are sensitive to heat and as the temperature increases, an exothermic reaction occurs which could result in the deflagration of the powder.

SUMMARY OF THE INVENTION

It is an object of the present invention to provide an azinphos-methyl wettable powder formulation which raises the temperature at which exothermic reaction occurs.

It is also an object of the present invention to provide a method for reducing the tendency of azinphos-methyl powder formulations to deflagrate at temperatures below 200° C.

It is a further object of the present invention to provide azinphos-methyl wettable powder formulations characterized by less intense deflagration at temperatures above 200° C.

These and other objects which will be apparent to those skilled in the art are accomplished by adding a carbonate of an alkali metal to the azinphos-methyl formulation in an amount such that the carbonate is at least 10% by weight of the total mixture.

DETAILED DESCRIPTION OF THE PREFERRED EMBODIMENTS OF THE INVENTION

The compositions of the present invention are composed of an insecticide powder formulation and a carbonate of an alkali metal. The insecticide powder formulation includes azinphos-methyl, known inert ingredients which are commonly used as carriers and known materials commonly used to promote dispersibility of the azinphos-methyl in water. Examples of such inert carriers and water dispersible promoting agents include: clays such as kaolin clay and attapulgite clay; amorphous silica; fumed silica; hydrated silica; naphthalene sulfonates; lignosulfonates; silicates such as magnesium silicate; sulfates; silicones and polyacrylates.

The carbonates of alkali metals useful in the present invention include carbonates and bicarbonates having an alkali metal as a component. Specific examples of suitable carbonates are: $NAHCO_3$, sodium aluminum carbonate, potassium carbonate and similar materials. Sodium hydrogen carbonate is preferred.

In the compositions of the present invention, the carbonate is included in an amount such that it will constitute at least 10% by weight, preferably from about 10 to about 50% by weight, and most preferably from about 30 to about 50% by weight of the total composition in dry form.

The compositions of the present invention may be diluted in accordance with techniques known in the art with quantities of water determined in accordance with the dosages recommended on the labels for the specific azinphos-methyl formulation being used.

The powder compositions of the present invention are characterized by deflagration at temperatures which are significantly higher than that of azinphos-methyl itself.

Having thus described our invention, the following Examples are given as being illustrative thereof. All weights and percentages given are parts by weight or percentages by weight, unless otherwise indicated.

EXAMPLES

1. Examples 1-6

Insecticide compositions containing the materials indicated in Table I in the relative amounts indicated in Table 1 were made by mixing the listed ingredients and mechanically milling. One gram samples of each of the mixtures were then placed in an aluminum dish on a hot plate. The temperature at which a reaction (detected as smoke) was observed was recorded. The results of this test are given in Table 2.

Examples 1, 5 and 6 are comparative basic azinphos-methyl formulation to which a carbonate or bicarbonate was not added. Examples 5 and 6 also illustrate azinphos-methyl formulations in which magnesium sulfate was substituted for the carbonate or bicarbonate of the present invention.

TABLE 1

| Ingredients (%) | Example | | | | | |
|---|---|---|---|---|---|---|
| | 1* | 2 | 3 | 4 | 5* | 6* |
| Azinphos-methyl[a] | 55.4 | 55.4 | 55.4 | 55.4 | 55.4 | 55.4 |
| Imsil A-10[b] | 4.0 | 4.0 | 4.0 | 4.0 | 4.0 | 4.0 |
| Petro-Morwet IP[c] | 3.0 | 3.0 | 3.0 | 3.0 | 3.0 | 3.0 |
| Polyfon H[d] | 3.0 | 3.0 | 3.0 | 3.0 | 3.0 | 3.0 |
| Barden Clay[e] | 8.0 | 8.0 | 8.0 | 8.0 | 8.0 | 8.0 |
| Zeolex 7A[f] | 24.6 | — | — | — | — | — |
| $NaAl(CO_3)_2$ | — | 24.6 | — | — | — | — |
| $K_2CO_3$ | — | — | 24.6 | — | — | — |
| $NaHCO_3$ | — | — | — | 24.6 | — | — |
| $MgSO_4$ | — | — | — | — | 24.6 | — |
| $MgSO_4\ 7H_2O$ | — | — | — | — | — | 24.6 |

[a]92% active ingredient
[b]Imsil A-10 is a amphorous silica sold by Illinois Mineral Company
[c]Petro-Morwet IP is a sodium diisopropyl naphthalene sulfonate sold by Desoto Inc.
[d]Polyfon H is a sodium lignosulfonate sold by Westvaco Chemical Division
[e]Barden Clay is a kolin clay sold by J.M. Huber Corporation
[f]Zeolex 7A is a hydrate silica sold by J.M. Huber Corporation
*Comparative

TABLE 2

| Example | Temperature @ which smoke was detected |
|---|---|
| 1 | 200° C. |

TABLE 2-continued

| Example | Temperature @ which smoke was detected |
|---|---|
| 2 | No smoke detected (heating discontinued at 316° C.) |
| 3 | No smoke detected (heating discontinued at 316° C.) |
| 4 | 254° C. |
| 5 | 188° C. |
| 6 | 188° C. |

Examples 7-13

Insecticide compositions containing the materials listed in Table 3 in the quantities indicated in Table 3 were made by mixing the listed ingredients by hand. One gram samples of each of the mixtures were then placed in an aluminum dish on a hot plate. The temperature at which deflagration occurred was observed and recorded. The results of these tests are given in Table 4. Example 7 illustrates a formulation in which the carbonate or bicarbonate required in the present invention was omitted. Example 7 is therefore comparative.

TABLE 3

| Ingredients (%) | Example | | | | | | |
|---|---|---|---|---|---|---|---|
| | 7* | 8 | 9 | 10 | 11 | 12 | 13 |
| Azinphos-methyl[a] | 55.4 | 55.4 | 55.4 | 55.4 | 55.4 | 55.4 | 55.4 |
| Imsil A-10[b] | 4.0 | 4.0 | 4.0 | 4.0 | 4.0 | 4.0 | 4.0 |
| Morwet IP[c] | 3.0 | 3.0 | 3.0 | 3.0 | 3.0 | 3.0 | 3.0 |
| Polyfon H[d] | 3.0 | 3.0 | 3.0 | 3.0 | 3.0 | 3.0 | 3.0 |
| Barden Clay[e] | 10.0 | — | — | — | — | — | — |
| Sodium Aluminum Carbonate | — | 10.0 | — | — | — | — | — |
| NAHCO$_3$ | — | — | 10 | 15 | 20 | 25 | 30 |
| Zeolex 7A[f] | 24.6 | 24.6 | 24.6 | 19.6 | 14.6 | 9.6 | 4.6 |

[a], [b], [c], [d], [e] and [f] have the same meanings as were given in Table 1.
*Comparative

TABLE 4

| Example | Temperature at which reaction was detected |
|---|---|
| 7 | 193° C. |
| 8 | 230° C. |
| 9 | 230° C. |
| 10 | 238° C. |
| 11 | 249° C. |
| 12 | 271° C. |
| 13 | No deflagration (heating discontinued at 316° C.) |

Samples of the formulations made in each of Examples 10-13 were evaluated on a Differential Scanning Calorimeter (DSC). These DSC scans indicated that the sodium bicarbonate was moderating the decomposition of the azinphos-methyl formulation. The higher the sodium bicarbonate content of the formulation, the greater the moderation effect. Sodium bicarbonate significantly reduced the total amount of exothermic energy developed in the formulation tested.

These scans suggest that the sodium bicarbonate acts as a heat sink and absorbs the energy of the exothermic decomposition of the azinphos-methyl.

Samples of the formulations made in each of Examples 7 (no carbonate or bicarbonate) and 10 (15% sodium bicarbonate) were evaluated on an Accelerated Rate Calorimeter (ARC). The results are given in Tables 5 (sample from Example 7) and 6 (sample from Example 10).

It can be seen from Tables 5 and 6 that the sample in which no carbonate or bicarbonate was included displayed an exotherm over a much shorter period of time (39.4 minutes when heated at a rate of 226.5° C./min.) than the sample containing 15% sodium bicarbonate. The results of the ARC scans confirmed the results of the DSC.

TABLE 5

| Sample: | Example 7 |
|---|---|
| Sample weight: (grams) | 0.5277 |
| Bomb weight: (grams) | 8.7894 |
| Thermal Inertia: | 13.9 |
| Bomb System Volume: (cm$^3$) | 8.8 |

| | 1st Exotherm |
|---|---|
| Exotherm Onset: (°C.) | 112.31 |
| Initial Self-Heat Rate: (°C/min) | 0.111 |
| Maximum Self-Heat Rate (°C./min) | 226.5 |
| Temperature at Heat-Rate Max: (°C.) | 138.2 |
| Initial Pressure: (psi) | 27.1 |
| Exotherm Duration: (minutes) | 39.4 |
| Final Temperature: (°C.) | 149.86 |
| Final Pressure: (psi) | 89.7 |
| Adiabatic Temperature Rise: (°C.) | 37.55 |
| Pressure Rise: (psi) | 62.6 |
| Pressure After Cool Down: (psi) | 69.5 |

TABLE 6

| Sample: | Example 10 |
|---|---|
| Sample weight: (grams) | 0.6425 |
| Bomb weight: (grams) | 8.7894 |
| Thermal Inertia: | 11.5 |
| Bomb System Volume: | 8.8 |

| | 1st Exotherm | 2nd Exotherm | 3rd Exotherm |
|---|---|---|---|
| Exotherm Onset: (°C.) | 101.40 | 145.21 | 157.59 |
| Initial Self-Heat Rate: (°C./min) | 0.022 | 0.021 | 0.050 |
| Maximum Self-Heat Rate: (°C./min) | 0.022 | 0.021 | 0.050 |
| Temperature at Heat-Rate Max: (°C.) | 101.40 | 145.21 | 157.59 |
| Initial Pressure (psi) | 35.2 | 63.4 | 67.0 |
| Exotherm Duration: (minutes) | 14.6 | 63.7 | 26.94 |
| Final Temperature: (°C.) | 101.76 | 145.6 | 159.37 |
| Final Pressure: (psi) | 38.5 | 63.7 | 69.9 |
| Adiabatic Temperature Rise: (°C.) | 0.36 | 0.39 | 1.78 |
| Pressure Rise: (psi) | 3.3 | 0.4 | 2.9 |
| Pressure After Cool Down: (psi) | — | — | 69.7 |

Samples of the formulations made in each of Examples 7 (no carbonate or bicarbonate) and 10 (15% sodium bicarbonate) were also evaluated using Thermogravimeter Analysis (TGA). The sample containing no carbonate or bicarbonate underwent a very rapid weight less at about 180° C. indicating rapid decomposition. The sample containing 15% sodium bicarbonate underwent a more gradual weight loss indicating gradual decomposition.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for raising the temperature at which deflagration and exothermic decomposition of azinphos-methyl powder formulations occurs comprising adding a carbonate of an alkali metal to the azinphos-methyl powder formulation in an amount such that at least 10% of the total mixture is the carbonate.

2. An insecticide composition having a raised deflagration temperature and a reduced tendency to undergo exothermic decomposition comprising a mixture of an azinphos-methyl powder formulation and a carbonate of an alkali metal in which at least 10% by weight of the total mixture is the carbonate.

3. The composition of claim 2 in which the sodium carbonate of the alkali metal is present in an amount of from about 10 to about 50% by weight.

4. The composition of claim 3 in which the carbonate is selected from the group consisting of sodium bicarbonate, sodium aluminum carbonate and potassium carbonate.

5. The composition of claim 4 in which the carbonate is sodium bicarbonate.

6. The composition of claim 2 in which the sodium bicarbonate of the alkali metal is present in an amount of from about 30 to about 50% by weight.

7. The composition of claim 6 in which the carbonate is selected from the group consisting of sodium bicarbonate, sodium aluminum carbonate and potassium carbonate.

8. The composition of claim 6 in which the bicarbonate is sodium bicarbonate.

* * * * *